United States Patent
Lobregt et al.

(10) Patent No.: US 8,290,225 B2
(45) Date of Patent: Oct. 16, 2012

(54) METHOD AND DEVICE FOR RELATING MEDICAL 3D DATA IMAGE VIEWING PLANES TO EACH OTHER

(75) Inventors: Steven Lobregt, Eindhoven (NL); Cornelis Pieter Visser, Eindhoven (NL); Hubrecht Lambertus Tjalling De Bliek, Eindhoven (NL); Paul Antoon Cyriel Desmedt, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1009 days.

(21) Appl. No.: 12/097,112

(22) PCT Filed: Dec. 6, 2006

(86) PCT No.: PCT/IB2006/054633
§ 371 (c)(1),
(2), (4) Date: Nov. 11, 2008

(87) PCT Pub. No.: WO2007/069144
PCT Pub. Date: Jun. 21, 2007

(65) Prior Publication Data
US 2009/0169076 A1    Jul. 2, 2009

(30) Foreign Application Priority Data
Dec. 14, 2005 (EP) ................... 05112143

(51) Int. Cl.
*G06K 9/30* (2006.01)
*G06K 9/36* (2006.01)

(52) U.S. Cl. ........ 382/128; 382/131; 382/154; 345/419; 600/425

(58) Field of Classification Search ......... 382/128–133; 600/407–464
See application file for complete search history.

(56) References Cited

U.S. PATENT DOCUMENTS

| 5,270,926 | A | * | 12/1993 | Tam ................. 378/4 |
| 5,458,111 | A | | 10/1995 | Coin |
| 5,638,819 | A | | 6/1997 | Manwaring et al. |
| 5,971,767 | A | * | 10/1999 | Kaufman et al. ......... 434/267 |
| 6,898,302 | B1 | * | 5/2005 | Brummer ............ 382/131 |
| 6,970,594 | B2 | * | 11/2005 | Williams ............ 382/154 |
| 7,496,222 | B2 | * | 2/2009 | Mussack et al. ......... 382/131 |
| 2005/0065424 | A1 | | 3/2005 | Shah et al. |

(Continued)

FOREIGN PATENT DOCUMENTS
EP    0922438 A1    6/1999
(Continued)

OTHER PUBLICATIONS

Peters, T.: "Image-Guided Surgery: From X-Rays to Virtual Reality"; Review From Computer Methods in Biomechanics and Biomedical Engineering, Imaging Research Laboratories, The John P. Robarts Research Institute, University of Western Ontario, London, Ontario, Canada, Chapter 3, vol. 2, SPIE press, 2000.

(Continued)

*Primary Examiner* — Melissa Koval
*Assistant Examiner* — Emily Chan

(57) ABSTRACT

A method of relating medical data image viewing planes to each other is provided. The method comprises defining at least two non-orthogonal two-dimensional (2D) image viewing planes in at least one three-dimensional (3D) medical image data set, and linking said 2D image viewing planes with a fixed relation to each other, such that when a first of said 2D image viewing planes is altered, the remaining 2D image viewing planes are automatically changed by said fixed relation with reference to said first 2D image viewing plane.

17 Claims, 3 Drawing Sheets

U.S. PATENT DOCUMENTS

2005/0078862 A1* 4/2005 Guillemaud et al. ......... 382/132
2005/0101864 A1* 5/2005 Zheng et al. ................. 600/443

FOREIGN PATENT DOCUMENTS

EP 1103229 A2 5/2001

OTHER PUBLICATIONS

Robb, R.: "Visualization in Biomedical Computing"; Parallel Computing, Elsevier Publishing, vol. 25, 1999, pp. 2067-2110.

Feng et al: "JAtlasView: A Java Atlas-Viewer for Browsing Biomedical 3D Images and Atlases"; BMC Bioinformatics, Biomed Central, London, Great Britain, vol. No. 6 Mar. 9, 2005, 7 Page Document.

Diallo et al: "VoxeLine: A Software Program for 3D Real-Time Visualization of Biomedical Images"; Computerized Medical Imaging and Graphics, Pergamon Press, vol. 22, No. 4, pp. 275-289, Jul. 20, 1998.

* cited by examiner

METHOD AND DEVICE FOR RELATING MEDICAL 3D DATA IMAGE VIEWING PLANES TO EACH OTHER

This invention pertains in general to the field of Medical Image Analysis. More particularly the invention relates to inspection of medical three dimensional (3D) data image sets, and even more particularly to the examination of 3D data image sets with multiple views, which are linked.

In the medical world it is common practice to inspect information of a single source or multiple sources using multiple views on said single source. For instance the 3D data in MR and CT is commonly inspected with slice examination or an orthoviewer, which shows the data from different views, each view being, rotated 90 degrees with respect to the others (orthogonal).

The analysis of data is currently shifting rapidly from classic viewing on film of 2 dimensional slide(s) towards computer supported viewing of the 3D data sets. As the data sets continuously get larger it also becomes increasingly important to use efficient ways to inspect this data.

Mainly three categories of 3D data viewing are currently available to the physician: 3D viewing, subsequent 2D slice viewing, combined 2D slice viewing as in for instance an orthoviewer or multiplanar reformat views, etc.

The classic viewing of slices is a transposition of the film viewing to a computer, but viewing all slices is time consuming and a full 3D insight is hard to obtain from such subsequent slice viewing.

The three dimensional viewing method is for 3D insight the ultimate method, but it is difficult to perform measurements on 3D views and overlapping structures often obscure the structures of interest. Thus many times an additional, often difficult and cumbersome operation, such as segmentation, is required to allow a proper view of the structure of interest.

2D slice viewing is currently still the most common solution. The drawback of subsequent 2D slice viewing is that it becomes cumbersome with large data sets and a 3D insight is difficult to achieve through this method.

For instance, a method of viewing cross-sections of a colon along its longitudinal length, based on 3D data sets, is disclosed in U.S. Pat. No. 5,458,111. A computer program calculates several individual cross sections of the colon along its longitudinal length at distances of 1-10 mm and saves the cross-sections in a memory, which later may be presented to a user. However, the views offered by this method suffer from the drawbacks mentioned in the previous paragraph.

The combined slice viewing method, e.g. in orthoviewer, multiplanar reformat views, etc., improves the 3D insight and also speeds up the examination of volumes. However a disadvantage of this combined slice viewing method is that the visualized planes are always perpendicular to each other. This configuration is maintained when the planes are rotated or translated. An orthoviewer is limited to one dataset at a time. Major disadvantages of the orthoviewer are that there are always three views and that the views are always perpendicular to each other. If inspection of more than one dataset at the same time is required, the same number of orthoviewers is needed, each having three views displayed at the same time. It is obvious that this increase of the number of views is not practically implementable due to limited screen size and human perception capability.

The current imaging systems, such as MRI, CT, etc, are based on 3D data imaging including 3 orthogonal planes X, Y and Z. With current viewing/comparing systems it is possible to view subsequent 3D data images, each from one specific angle. A disadvantage of the current linked view methods, is that the geometrical relation between the viewed planes is a transformation matrix required to fit one dataset to the other. The current methods used assume that the viewed planes show the same cross-section through the data, despite of the fact that both have different geometries. This assumption results in undesired restrictions.

Hence, there is a need for a new technical solution which improves the overall performance when viewing 3D data images, which are related to each other. More precisely, there is a need for a more advantageous method allowing for combined viewing of a plurality of 2D images derived from a 3D image data set. Advantageously, an arbitrary geometrical relation between the images is maintained. Further, it would be advantageous if some embodiments may provide further information derived from the plurality of 2D images.

Hence, an improved method of presenting a plurality of 2D images would be advantageous allowing for increased flexibility.

Accordingly, the present invention preferably seeks to mitigate, alleviate or eliminate one or more of the above-identified deficiencies in the art and disadvantages singly or in any combination and solves at least the above mentioned problems related to the above-mentioned prior art by providing a method, a computer-readable medium comprising a computer program, and a medical workstation according to the appended patent claims.

According to a first aspect of the invention, a method is provided for relating medical data image viewing planes to each other. The method comprises defining at least two non-orthogonal two-dimensional (2D) image viewing planes in at least one three-dimensional (3D) medical image data set, and linking said 2D image viewing planes to each other, such that when a first of said 2D image viewing planes is repositioned, each of said remaining 2D image viewing planes are automatically repositioned with reference to said repositioned first 2D image viewing plane.

According to a further aspect of the invention, a computer-readable medium having embodied thereon a computer program for relating medical data image viewing planes to each other for processing by a computer. The computer program comprises a first code segment for defining at least two non-orthogonal two-dimensional (2D) image viewing planes in at least one three-dimensional (3D) medical image data set, and a second code segment for linking said 2D image viewing planes to each other, such that when a first of said 2D image viewing planes is repositioned, each of said remaining 2D image viewing planes are automatically repositioned with reference to said repositioned first 2D image viewing plane.

According to yet another aspect of the invention, a medical workstation is provided. The medical workstation configured to perform the method according to a first aspect of the invention, and is adapted to relate medical data image viewing planes to each other. The medical workstation comprises means for defining at least two non-orthogonal two-dimensional (2D) image viewing planes in at least one three-dimensional (3D) medical image data set, and means for linking said 2D image viewing planes to each other, such that when a first of said 2D image viewing planes is repositioned, each of said remaining 2D image viewing planes are automatically repositioned with reference to said repositioned first 2D image viewing plane.

The present invention is advantageous over the prior art as it for instance enhances the inspection of data set(s) because the linked relation between 2D data sets drastically increases the flexibility for data inspection.

These and other aspects, features and advantages of which the invention is capable of will be apparent and elucidated from the following description of embodiments of the present invention, reference being made to the accompanying drawings, in which FIG. 1 is a schematic view illustrating an orthoviewer with viewing planes perpendicular to each other;

The following description focuses on embodiments of the present invention applicable to specific examples for medical images, and in particular to a vessel region or a skull region. However, it will be appreciated that the invention is not limited to these specific applications but may be applied to many other applications, including for example intestinal regions etc.

The present invention provides an advantageous way of inspecting 3D image data sets with linked 2D views.

Moreover the present invention provides a convenient future-proof way of handling data sets as data sets are continuously getting larger and contain data from more and more different information sources.

Embodiments of the present method extend the relation nature of the different views on the data set(s) and are therefore an extension of combined slice viewing. Different additional transformations may be imposed according to different embodiments, in order to inspect data sets.

Figure 1:
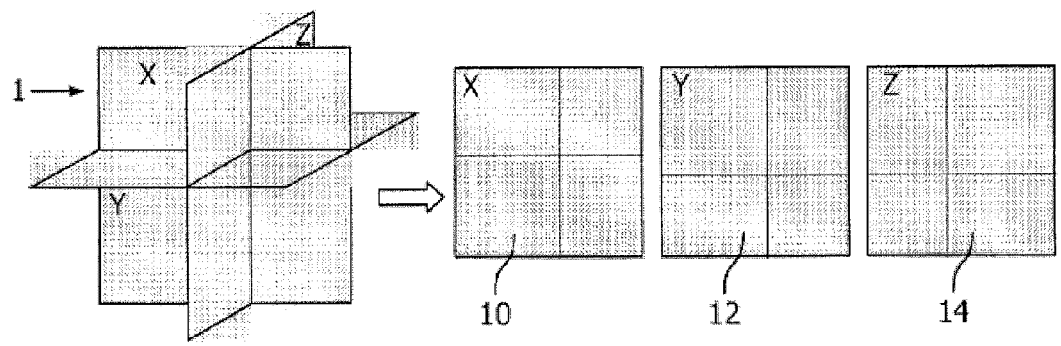

FIG. 1 illustrates an orthoviewer with viewing planes perpendicular to each other. Currently, the so called orthoviewer is a commonly used method for simultaneous displaying and viewing of multiple cross-sections through a 3D dataset, thus providing an increased understanding of the 3D structures inside the investigated data volume. In FIG. 1 the orthogonal relation in three-dimensional (3D) space between the planes X, Y, Z is visualized on the left at 1. The resulting two-dimensional (2D) views 10 (X-plane), 12 (Y-plane), and 14 (Z-plane) are shown to the right of FIG. 1 and show the visualized viewing planes corresponding to the cut-planes through the X, Y, Z planes, respectively. A disadvantage of this method is that the visualized planes 10, 12, 14 are always perpendicular to each other. This configuration is maintained when the planes are rotated or translated. An orthoviewer is limited to one dataset at a time. In terms of medical images, this implies that orthogonal cross-sections through the same volume are made for a 2D representation of volumetric representations. The relation between the planes is fixed orthogonal. Obvious disadvantages of the orthoviewer are that there are always three views and that the views are always perpendicular to each other. If inspection of more than one dataset at the same time is required, a multiple number of orthoviewers is needed. These orthoviewers should then be linked like described from the registered single views below. However, the use of multiple orthoviewers quickly becomes confusing for the user due to the amount of offered information, so that the information that the user tries to extract from the images is rather concealed than presented.

Figure 2:
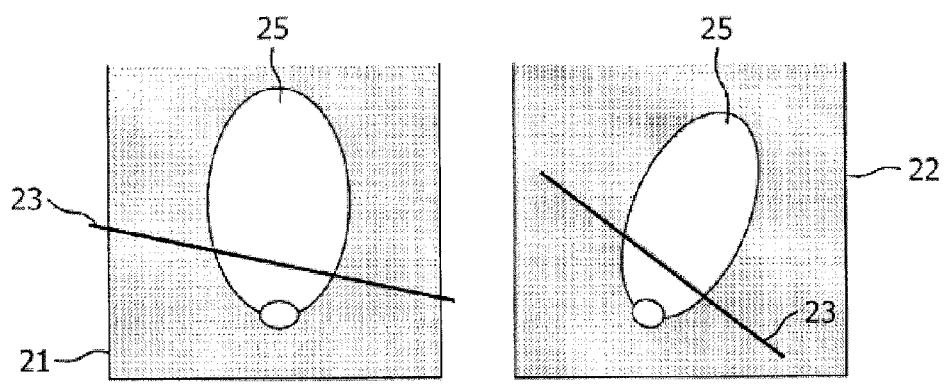
FIG. 2 is a schematic view illustrating registered views.

FIG. 2 illustrates a method of registered views, wherein the viewing plane 23 shows corresponding anatomy from two datasets 21 and 22. For instance data set 21 may be acquired from a first imaging modality, such a as a CT, at a first instance, and dataset 22 may be acquired from a second image modality, e.g. an MR, at a later instance. The plane positions are related through a transformation matrix derived from the content of these datasets, and/or from additional information that was stored with the datasets by the data acquisition device at the time of acquisition of the data. When two datasets, such as datasets 21, 22 need to be compared or inspected at the same time, one approach is to use registered views. This may for instance concern two datasets of the same anatomy but acquired with different modalities to get complementary information. Another possibility is that the same anatomy is scanned with the same modality but at different points in time to get information about the progress of a disease or therapy. In any case the targeted anatomy will not be acquired with the same geometry. In this case a transformation matrix between the datasets is determined based on positions of corresponding landmarks, pixel similarity measures, or the like. In short registration of the datasets. The transformation matrix may be used to position a cross-sectional plane in one dataset on a position and orientation that corresponds to the position and orientation of a cross-sectional plane in the other dataset. The purpose is to view two planes with corresponding anatomical information from two different datasets. The relation between the cutplanes 23 and the patient 25 is fixed.

When the position or orientation of one of these registered viewing planes is modified, for instance translated, rotated, or zoomed, then the other viewing plane is automatically also repositioned to the corresponding position in the other dataset according to the used transformation matrix.

Figure 3:
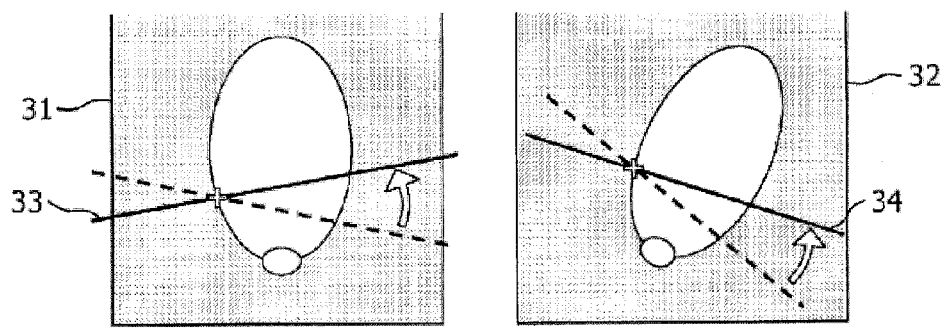
FIG. 3 is a schematic view illustrating how a repositioning of one viewing plane relates to a corresponding repositioning of the other plane, according to prior art.

FIG. 3 illustrates registered views 31 and 32, wherein repositioning of one viewing plane 33 leads to a corresponding repositioning of the other plane 34.

The disadvantage of these linked view methods is that the geometrical relation between the viewed planes is the transformation matrix required to fit one dataset to the other. The assumption in current linked view methods is that the viewed planes show the same cross-section through the data, despite of the fact that both datasets have different geometries.

The following description focuses on an embodiment of the present invention applicable to a 3D image analysis system and in particular to 3D data images within healthcare. However, it will be appreciated that the invention is not limited to this application but may be applied to many other 3D image analysis systems in other fields than healthcare.

An embodiment of the method of the present invention comprises an addition of a general transformation matrix, including translation, rotation, scaling, etc., between different views. This allows for instance to inspect a data set with two linked views which are translated to each other, rotated with arbitrary angle to each other, etc. The transformation matrix is further extended to arbitrary relations between different views, and it has capability to depend on information present in the images, location information, path information. The extension of the transformation matrix is valid for the examination of data from a single source as well as for data from multiple sources. The relation between the views is not necessarily the transformation between two similar but may be between geometrically different datasets, and the purpose is not to view the same or corresponding cross-sections in these linked views, but cross-sections that are linked in another way.

Figure 4:
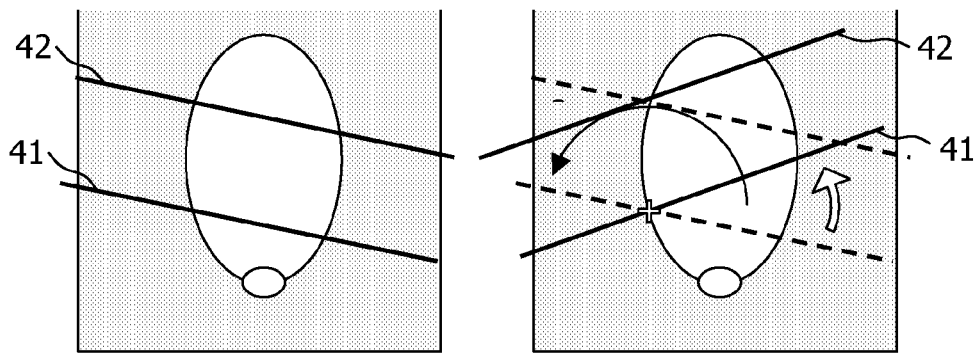
FIG. 4 is a schematic view illustrating an embodiment of the method of the present invention to relate two viewing planes to each other, by correlating the orientation and distance of the two viewing planes to a cylindrical radius.

In a first embodiment of the invention according to FIG. 4, the method is visualized by means of two viewing planes 41 and 42 which are linked by a defined relation that is maintained during repositioning of said viewing planes (on the right in FIG. 4). The relation is defined and maintained between viewing plane 41 and 42 in FIG. 4. As can be seen the relation behavior differs from the behavior as described in FIG. 3. Viewing plane 41 and 42 in FIG. 4 do not represent the same cross-section and when viewing plane 41 is repositioned, viewing plane 42 does not reposition in the same manner. As can further be observed in FIG. 4, when viewing plane 41 rotates around a point (shown as a cross in FIG. 4), or more precisely around a line in 3D, viewing plane 42 will not simply rotate around the line but it will describe a trajectory that is tangential to a cylindrical surface with radius equal to the distance between the planes.

An example of an application which may benefit from the behavior of the above-described embodiment is the determination of a trajectory for intervention. One can freely move a cross-sectional plane around through a 3D dataset of the relevant volume and see not only the current cross-section but also one or more cross-sections which are located a certain distance 'ahead'. For instance, when entering a surgical instrument through a keyhole during a minimal invasive procedure, often structures need to be avoided on the passage of the instrument into the body towards a target area. It is known to use X-Ray monitoring during insertion of such surgical instruments. In this case bones and instruments are visible on the X-Ray image. However, it is often more important to avoid other structures than bones, namely soft tissues that do not show up on X-Ray images, like blood vessels, for instance in the head. Hence, a position for the opening in the skull has to be determined such that a 'safe' path from the opening to the target area, for instance a tumor, is possible. While inserting the instruments, a continuous checking of the volume ahead of the instrument tip prevents serious damage that otherwise would be caused by collision with and possibly rupture of blood vessels. By visualizing a cross-section a certain distance 'ahead' in insertion direction of the instrument, such critical structures may be discovered before the instrument comes near the structure, and the structure may be circumvented by changing the insertion direction of the instrument. This ensures to safely reach the desired treatment site with the distal end of the surgical instrument inside the body.

In another embodiment of the present invention, instead of the two viewing planes being represented by the same dataset, the two viewing planes are represented by two different datasets.

In yet another embodiment of the present invention the number of viewing planes is represented by an equal number of datasets.

Another embodiment of the invention relates to determination of entry paths for instruments that need to be inserted with a preferred angle between them. The relation between two viewing planes is here a configuration in which two planes cross each other under a certain angle, which can be used to determine the entry paths for the instruments at the same time. For instance, an endoscope is introduced through a keyhole towards a treatment site, where e.g. a tumor is to be removed. A surgical instrument is introduced through another keyhole towards the treatment site, but at another angle than the endoscope. According to other embodiments different instruments than endoscopes might be visualized within the scope of the present invention.

The extended transformation matrix of some embodiments of the present invention, which provides new ways of relating the viewing planes, enables besides from a rigid relation, described in the above embodiments, relations which may also depend on other criteria. According to some embodiments, the criteria for the relation between viewing planes may have no relation to the geometry of the dataset(s) at all. An example of such a relation is for instance that two viewing planes are parallel to each other with a certain distance in between. This relation is maintained when one of the planes is repositioned.

Figure 5:
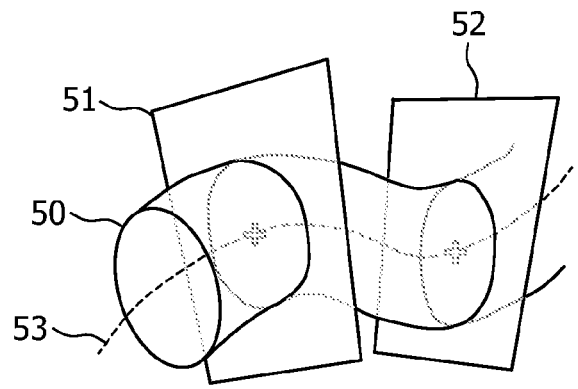
FIG. 5 is a schematic view illustrating another embodiment of the method of the present invention to relate two viewing planes to each other, in this case perpendicular to the centerline of a tubular structure and with a constant distance between the two viewing planes.

Another embodiment of the present invention, illustrated with reference to FIG. 5, describes a transformation matrix capable of establishing a non-fixed relation between viewing planes 51 and 52, which are perpendicular to a path 53, the relation being defined as a distance along the path. More precisely, the linking relation between different views is based on a relation between a local geometry of the path and the cutplanes of the views. In the example of FIG. 5, the path 53 is defined as following a centerline of a tubular structure 50. When one plane perpendicular to the path is repositioned, resultantly the other plane perpendicular to the path 53 is repositioned in a way that the distance between the planes along the path 53 is maintained. Because path 53 will be curved and the planes will be perpendicular to path 53, the orientation of one plane with respect to the other will vary, i.e. only the distance along the path 53 will be maintained.

The method of the invention furthermore enables presenting the information on a human-readable device. The human-readable device is able to display the information from the investigated viewing planes and may include at least an additional view, in which image analysis calculations of the investigated viewing planes may be presented. Examples are given in FIGS. 6, 7 and 8, described hereinafter.

The image analysis calculations may include any common image analysis calculation such as, but not limited to, subtraction, filtering, intensity division, thresholding, edge detection, corner detection, structure identification, coloring, or any combination thereof. A subtraction image of the views gives a very clear indication whether the cross-sectional area of a tubular structure is constant, decreasing or increasing, and how fast the area changes when moving along the path, simply by the sign and magnitude of the local difference.

Figure 6:
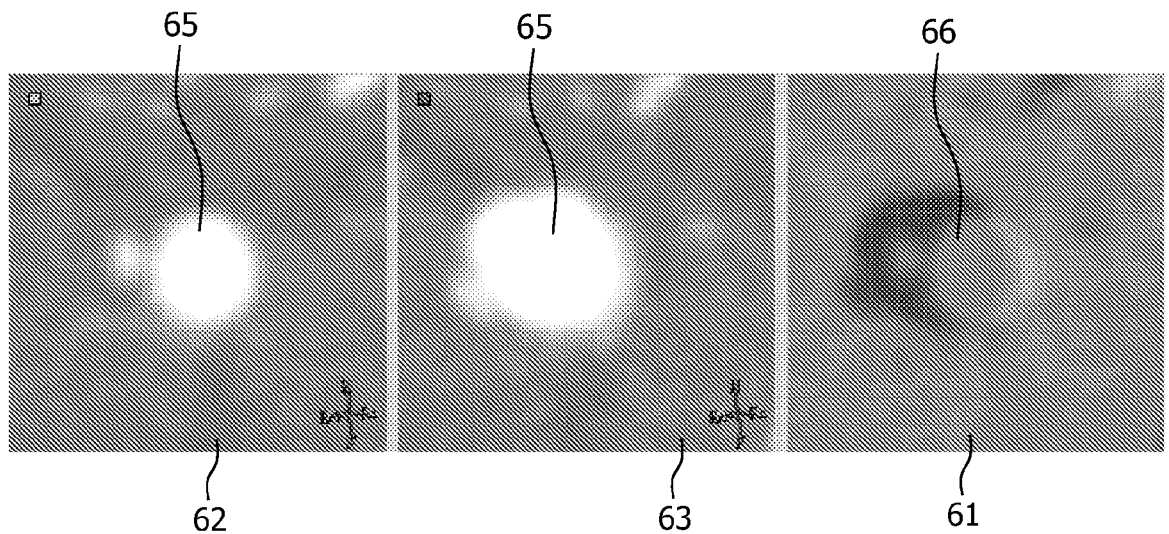
FIG. 6 is a series of images showing an example of presenting two related viewing planes and additional information derived thereof on a human-readable device, concerning a tubular structure, similar to that shown in FIG. 5.

In FIG. 6, two images of a cutplane view through a tubular structure (vessel) 65 illustrate an exemplary investigation based on the above mentioned method described with reference to FIG. 5, i.e. the relation between the two views 62, 63 is defined as a distance along the path along the centerline of vessel 65. In the additional view 61 a resulting subtraction image of view 62 and 63 can be observed. This information can be updated in real time as the planes are interactively being repositioned. In this way it is for instance easy to detect stenosis of a vessel. In this case information offered in the additional view allows to detect any changes in vessel diameter. Furthermore, the gradient of the change, i.e. how fast the diameter changes is provided. Thus, one may detect stenosis of a vessel by providing a pre-defined threshold for this gradient. When the threshold is crossed, this is an indication for a pathological stenosis.

Figure 7:
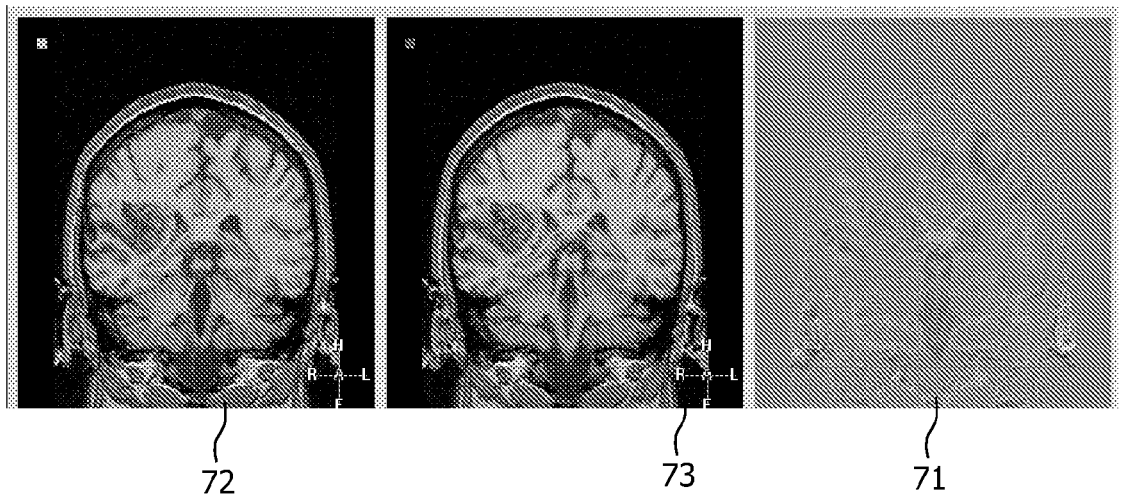
FIG. 7 is a series of images showing an example of presenting viewing planes and additional information derived thereof on a human-readable device, with reference to a skull region including the human brain.
Figure 8:
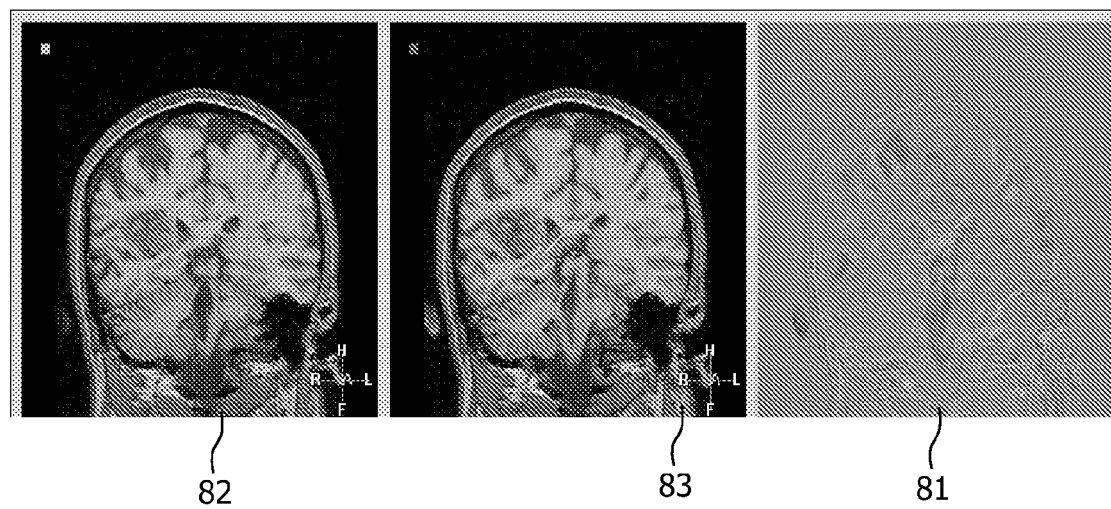
FIG. 8 shows another example of presenting the viewing planes, slightly rotated compared to FIG. 7, and comparing information, concerning the human brain, on a human-readable device.

FIG. 7 and FIG. 8, illustrate the additional view by means of a further example. The additional view that is displayed on a human-readable device describing a resulting image of an image analysis calculation performed on the investigated image views 72, 73, 82, 83, is a subtraction of image view 72, 82 and image view 73, 83 respectively. FIG. 7 depicts view 72, 73, which are slices through a human skull and illustrate a human brain. The additional view 71 shows the resulting image after subtracting view 72 with 73. In FIG. 8 the views 82, 83 are slightly rotated compared to FIG. 7 and the resulting image is showed in the additional view 81.

One possible application of embodiments of the present invention is for automized determination of pathological disorders. For instance, the above-mentioned stenosis detection may be automated. In this case the local curvature of the vessel is measured, which enables detection of the anatomical path of the vessel, and definition of a centerline through the vessel. Subsequently an automated analysis of the relation of two views along the centerline and perpendicular thereto may be performed. The difference (subtraction) between the views, i.e. the intensity (grey values) and density of the subtracted pixels thereof indicate the presence of a stenosis along the path of the vessel. This enables a closer examination of the identified stenosis.

The method of the invention may be implemented in any suitable form including hardware, software, firmware or any combination of these. However, preferably, the image analysis calculations, such as the transformation matrix, and the presenting of information is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Applications and use of the above-described method of relating medical 3D data image viewing planes in a new manner according to the invention are various and include all fields wherein medical 3D data is processed.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method of relating medical data image viewing planes to each other, wherein said method comprises:
  defining, by a computer processor, at least two non-orthogonal two-dimensional (2D) image viewing planes in at least one three-dimensional (3D) medical image data set, and
  linking, by the computer processor, said 2D image viewing planes to each other, such that when a first of said 2D image viewing planes is repositioned, each of said remaining 2D image viewing planes are automatically repositioned with reference to said repositioned first 2D image viewing plane,
  wherein said linking comprises a general transformation matrix, and
  wherein said transformation matrix defines a relation between the viewing planes in a non-geometrical manner that is specifically oriented to a structure and follows an arbitrary trajectory between the viewing planes, wherein the viewing planes are separated by a distance.

2. The method according to claim 1, wherein the transformation matrix includes translation, rotation, scaling, between the different 2D image viewing planes.

3. The method according to claim 2, said transformation matrix providing arbitrary relations between different 2D image viewing planes.

4. The method according to claim 2, said transformation matrix depending on information present in the data images such as location information and path information.

5. The method according to claim 1, wherein said orientation is orthogonal to a center line of said structure, which is a tubular structure, and said distance is following the center line of said tubular structure.

6. The method according to claim 1, wherein the 2D image viewing planes are presented on a human-readable device, including an additional view describing an image analysis calculation of said 2D image viewing planes.

7. A method according to claim 6, wherein said image analysis calculation contains general image analysis calculations such as, subtraction, filters, intensity division, thresholding, edge detection, corner detection, structure identification, coloring or any combination thereof.

8. The method according to claim 1, wherein during repositioning of the at least two 2D image viewing planes a predetermined relationship between the at least two 2D image viewing planes remains constant.

9. A method of relating medical data image viewing planes to each other, wherein said method comprises:
  defining, by a computer processor, at least two non-orthogonal two-dimensional (2D) image viewing planes in at least one three-dimensional (3D) medical image data set, and
  linking, by the computer processor, said 2D image viewing planes to each other, such that when a first of said 2D image viewing planes is repositioned, each of said remaining 2D image viewing planes are automatically repositioned with reference to said repositioned first 2D image viewing plane,
  wherein said linking comprises a general transformation matrix, and
  wherein said transformation matrix geometrical relation between said viewing planes is described by, when a point in the dataset of the first viewing plane is changed, the corresponding point in the dataset of the second viewing plane is moved into a new position on a cylindrical trajectory of a fixed radius with a center point in the originating point of said dataset of said first viewing plane.

10. The method according to claim 9, wherein said transformation matrix relation between the viewing planes, in a geometrical manner is a fixed angle between said viewing planes.

11. A medical workstation configured to perform the method according to claim 1, adapted to relate medical data image viewing planes to each other, comprising:
  means for defining at least two non-orthogonal two-dimensional (2D) image viewing planes in at least one three-dimensional (3D) medical image data set, and
  means for linking said 2D image viewing planes to each other, such that when a first of said 2D image viewing planes is repositioned, each of said remaining 2D image viewing planes are automatically repositioned with reference to said repositioned first 2D image viewing plane,
wherein said linking comprises a general transformation matrix, and
wherein said transformation matrix defines a relation between the viewing planes in a non-geometrical manner that is specifically oriented to a structure and follows an arbitrary trajectory between the viewing planes, wherein the viewing planes are separated by a distance.

12. The medical workstation according to claim 11, wherein during repositioning of the at least two 2D image viewing planes a predetermined relationship between the at least two 2D image viewing planes remains constant.

13. A non-transitory computer-readable medium having embodied thereon a computer program for relating medical data image viewing planes to each other for processing by a computer, the computer program comprising:
   a first code segment for defining at least two non-orthogonal two-dimensional (2D) image viewing planes in at least one three-dimensional (3D) medical image data set, and
   a second code segment for linking said 2D image viewing planes to each other, such that when a first of said 2D image viewing planes is repositioned, each of said remaining 2D image viewing planes are automatically repositioned with reference to said repositioned first 2D image viewing plane,
   wherein said linking comprises a general transformation matrix, and
   wherein said transformation matrix defines a relation between the viewing planes in a non-geometrical manner that is specifically oriented to a structure and follows an arbitrary trajectory between the viewing planes, wherein the viewing planes are separated by a distance.

14. The non-transitory computer readable storage mediun according to claim 13,
   wherein during repositioning of the at least two 2D image viewing planes a predetermined relationship between the at least two 2D image viewing planes remains constant.

15. A method of computer assisted detection and diagnosis of locations in a body that may show conditions which are outside normal variation, comprising:
   indicating at least one location that can be suspected of such possible conditions, and presenting these locations as locations that need further investigation, wherein said detection comprises:
      defining at least two non-orthogonal two-dimensional (2D) image viewing planes in at least one three-dimensional (3D) medical image data set,
      linking said 2D image viewing planes to each other, such that when a first of said 2D image viewing planes is repositioned, each of said remaining 2D image viewing planes are automatically repositioned with reference to said repositioned first 2D image viewing plane;
      automatically repositioning said first 2D image viewing plane along a path in the body, and
      deriving information for said detection and diagnosis from differences between image information from said first 2D image viewing plane and the remaining 2D image viewing planes along said path.

16. Method according to claim 15, comprising computer assisted detection and diagnosis of stenosis, comprising:
   measuring a local curvature of a vessel,
   detecting an anatomical path of the vessel, and
   defining a center line through the vessel; and subsequently performing an automated analysis of the relation of two views along the centerline and perpendicular thereto, and detecting a stenosis from a intensity and density of subtracted pixels between the two views, thus indicating the possible presence of a stenosis along the path of the vessel when said intensity and density subtracted pixels exceeds a pre-defined threshold.

17. The method according to claim 15, wherein during repositioning of the at least two 2D image viewing planes a predetermined relationship between the at least two 2D image viewing planes remains constant.

* * * * *